United States Patent [19]

Stinski

[11] Patent Number: 5,385,839
[45] Date of Patent: * Jan. 31, 1995

[54] TRANSFER VECTORS AND MICROORGANISMS CONTAINING HUMAN CYTOMEGALOVIRUS IMMEDIATE-EARLY PROMOTER REGULATORY DNA SEQUENCE

[75] Inventor: Mark F. Stinski, Iowa City, Iowa

[73] Assignee: University of Iowa Research Foundation, Iowa City, Iowa

[*] Notice: The portion of the term of this patent subsequent to Dec. 1, 2009 has been disclaimed.

[21] Appl. No.: 900,056

[22] Filed: Jun. 17, 1992

Related U.S. Application Data

[63] Continuation of Ser. No. 582,130, Sep. 10, 1990, Pat. No. 5,168,062, which is a continuation of Ser. No. 256,134, Oct. 5, 1988, abandoned, which is a continuation of Ser. No. 58,662, May 22, 1987, abandoned, which is a continuation of Ser. No. 696,617, Jan. 30, 1985, abandoned.

[51] Int. Cl.$^6$ .......................... C12N 5/10; C12N 1/21; C12N 15/70; C12N 15/85
[52] U.S. Cl. ................ 435/240.2; 435/69.1; 435/252.3; 435/252.33; 435/320.1
[58] Field of Search ................. 435/320.1, 69.1, 240.2, 435/172.3, 252.3, 252.33; 536/27; 935/33, 34, 39, 41, 43

[56] References Cited

U.S. PATENT DOCUMENTS

5,168,062  1/1992  Stinski .............................. 435/240.2

FOREIGN PATENT DOCUMENTS

173177  3/1986  Austria.

OTHER PUBLICATIONS

Smith et al., Mol. and Cell. Biol., vol. 3, No. 12, pp. 2156–2165 (1983).
Greenaway et al., "Human cytomegalovirus DNA: BamHI, EcoRI and PstI restriction endonuclease cleavage maps," *Gene* 18:355–360, 1982.
Jahn et al., "Predominant Immediate-Early Transcripts of Human Cytomegalovirus AD 169," *Journal of Virology*, 49(2):363–370, 1984.
Foecking and Hofstetter, *Gene* 45:101–105, 1986.
Wasyyk, B. et al., *EMBO* 2:1605–1611, 1983.
Stinski, M. et al., *Journal of Virology* 46:1–14, 1983.
Stinski, M. et al., *J. Gen. Virol.* 43:119–129, 1979.
Stinski, M. et al., *Journal of Virology* 31:231–239, 1979.
Wathen, M. et al., *Journal of Virology* 41:462–477, 1982.
Stinski, M. F., *Journal of Virology* 19:594–609, 1976.
Manley, J. L. et al., *Proc. Natl. Acad. Sci. U.S.A.* 77:3855–3859, 1980.
Thomsen, D. R. et al., *Proc. Natl. Acad. Sci. U.S.A.* 81:659–663, 1984.
Stenberg, R. M. et al., *Journal of Virology* 49:190–199, 1984.
de Villier, J. et al., *Nucleic Acids Research* 9:6251–6264, 1981.
Rosenthal, N. et al., *Science* 222:749, 755, 1983.
Levinson, B. et al., *Nature* 295:568–572, 1982.
Thomsen et al., *Gene* 16:207–216, 1981.
Berk, A. J. et al., *Cell* 12:721–732, 1977.
Weeks, D. L. et al., *Molecular and Cellular Biology* 3:1222–1234, 1983.
Lusky, M. et al., *Molecular and Cellular Biology* 3:1108–1122, 1983.
Queen, C. et al., *Cell* 33:741–748, 1983.
Banerji, J. et al., *Cell* 33:729–740, 1983.
Gillies, S. D. et al., *Cell* 33:717–728, 1983.

(List continued on next page.)

*Primary Examiner*—Richard A. Schwartz
*Assistant Examiner*—David Guzo
*Attorney, Agent, or Firm*—Seed and Berry

[57] ABSTRACT

The cloning of a eucaryotic promoter-regulatory region that functions preferentially in human cells is disclosed. The invention is exemplified by the cloning of a section of the human cytomegalovirus genome comprising a DNA sequence with regulatory and promoter signals and an initiation site for RNA synthesis. The fragment, termed the human cytomegalovirus (HCMV) promoter-regulatory sequence, was obtained from purified HCMV DNA.

7 Claims, 3 Drawing Sheets

OTHER PUBLICATIONS

Luciw, P. A. et al., *Cell* 33:705–716, 1983.
Hearing, P. et al., *Cell* 33:695–703, 1983.
Chandler, V. L. et al., *Cell* 33:489–499, 1983.
Chambon, P. et al., *Annual Rev. Biochem.* 50:349–383, 1981.

Stinski, M. F. et al., Ninth International Herpesvirus Workshop, Aug. 1984 (University of Washington).
Stinski, M. F. et al., 6th Cold Spring Harbor Meeting on Herpersvirus, Aug. 1982, Cold Spring Harbor Laboratories, Cold Spring Harbor, New York.

```
                                                          (5') GGCGACCGCC  -480

CAGCGACCCC CGCCCGTTGA CGTCAATAGT GACGTATGTT CCCATAGTAA CGCCAATAGG  -420

GACTTTCCAT TGACGTCAAT GGGTGGAGTA TTTACGGTAA ACTGCCCACT TGGCAGTACA  -360

TCAAGTGTAT CATATGCCAA GTCCGCCCCC TATTGACGTC AATGACGGTA AATGGCCCGC  -300

CTAGCATTAT GCCCAGTACA TGACCTTACG GGAGTTTCCT ACTTGGCAGT ACATCTACGT  -240

ATTAGTCATC GCTATTACCA TGGTGATGCG GTTTTGGCAG TACACCAATG GGCGTGGATA  -180

GCGGTTTGAC TCACGGGGAT TTCCAAGTCT CCACCCCATT GACGTCAATG GGAGTTTGTT  -120

HincII
TTGGCACCAA AATCAACGGG ACTTTCCAAA ATGTCGTAAT AACCCCGCCC CGTTGACCCA  -60
                                                 SacI         +1
AATGGGCGGT AGGCGTGTAC GGTGGGAGGT CTATATAGCA GAGCTCGTTT AGTGAACCGT  (3')
                                                              Cap
```

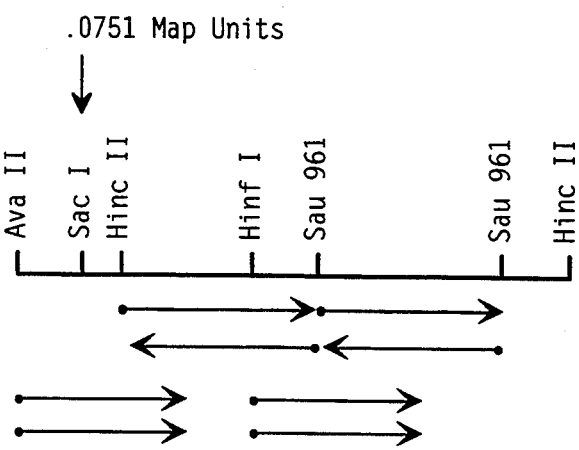

FIG. 1

Consensus for a 19 base pair repeat

5' CCCC$\frac{A}{G}$TTGACGTCAATGGG 3'

-72  CCCCGTTGACGcAAATGGG  -54

-146 CCCCATTGACGTCAATGGG  -128

-334 CCCCtATTGACGTCAATGAc  -314

-468 GCCCGTTGACGTCAATAGT  -450

Consensus for a 18 base pair repeat

5' $\frac{C}{A}$CTAACGGGACTTTCCAA 3'

-108 AtCAACGGGACTTTCCAA  -91

-171 ACTcACGGGgATTTCCAA  -154

-276 CCTtACGGGAgTTTCCtA  -259

-427 CCAAtAGGGACTTTCCAt  -410

Consensus for a 16 base pair repeat

5' CTTGGCAGTACATCAA 3'

-371 CTTGGCAGTACATCAA  -356

-291 ATGCCCAGTACATGAC  -276

-258 CTTGGCAGTACATCTA  -243

-207 TTTGGCAGTACACCAA  -192

21 base pair repeat

-509 ACGGTAAATGGCCCGCCTGGC  -489

-316 ACGGTAAATGGCCCGCCTGGC  -296

FIG. 3

TRANSFER VECTORS AND MICROORGANISMS CONTAINING HUMAN CYTOMEGALOVIRUS IMMEDIATE-EARLY PROMOTER REGULATORY DNA SEQUENCE

This invention was made with Government support under Grant No. AI13526 awarded by the National Institute of Allergy and Infectious Diseases. The Government has certain rights in this invention.

CROSS-REFERENCE TO PRIOR APPLICATIONS

This application is a continuation of U.S. patent application Ser. No. 07/582,130, filed Sep. 10, 1990, now U.S. Pat. No. 5,168,062; which was a continuation of U.S. patent application Ser. No. 07/256,134, filed Oct. 5, 1988, now abandoned; which was a continuation of U.S. patent application Ser. No. 07/058,662, filed May 22, 1987, now abandoned; which was a continuation of U.S. patent application Ser. No. 06/696,617, filed Jan. 30, 1985, now abandoned.

BACKGROUND OF THE INVENTION

The invention herein is exemplified by the cloning of a deoxynucleotide sequence possessing regulatory signals which are recognized preferentially by human cell factors involved in transcription by RNA polymerase II. The subject DNA sequence, or enhancer, provides a promoter-regulatory region to enhance the expression of an adjacent gene in eucaryotic cells of human origin.

Enhancers have been found in various animal viruses such as polyoma virus, BK virus, adenovirus, simian virus 40, Moloney sarcoma virus, bovine papilloma virus, and Rous sarcoma virus (deVillier and Schaffner, Nucl. Acids Res. 9:6251–6264, 1981; Rosenthal et al., Science 222:749–755, 1983; Hearing and Shenk, Cell, 33:695–703, 1983; Weeks and Jones, Mol. Cell, Biol. 3:1222–1234, 1983; Levinson et al., Nature 295:568–572, 1982; Luciw et al., Cell 33:705–716, 1983. Enhancer elements have also been found to occur in immunoglobulin genes (Banerji et al., Cell 33:729–749, 1983; Gillies et al., Cell 33:717–728, 1983; Queen and Baltimore, Cell 33:741–748, 1983).

Gene activation can be mediated in a host-specific and/or tissue-specific manner (deVilliers and Schaffner, Nucl. Acids Res. 9:6251–6254, 1981. Queen and Baltimore, Cell 33:741–748, 1983). It is assumed that host cell factors involved in transcription interact with the DNA sequence containing the enhancing element by an unknown mechanism. By definition, an enhancer can influence downstream gene expression while present in either orientation and at various distances up to 4 kilobases from the enhanced gene (Chambon and Breathnack, Annual Rev. Biochem. 50:349–383, 1981).

Human cytomegalovirus (HCMV), a member of the herpes virus classification group, has a large double-stranded DNA genome of 240 kilobases (kb). The viral genome consists of a long and short unique region flanked by different repeat sequences that are inverted relative to each other. Four genome arrangements, resulting from the possible combination of inversions of the two sections of the genome, are present in DNA preparations in approximately equal amounts.

At immediate early (IE) times after infection—i.e., in the absence of de novo viral protein synthesis, 88% or more of the viral RNA originates from a region in the long unique component of the viral genome between 0.660 and 0.751 map units for the Towne strain of HCMV. One or more of the IE viral genes presumably codes for a vital regulatory protein that stimulates transcription from other regions of the viral genome.

Based on the high steady-state levels of viral mRNA and the abundance of its translation product in the infected cell, the IE gene between 0.739 and 0.751 map units is highly expressed and has been designated IE region 1 or the major IE gene. Adjacent IE genes from 0.732 to 0.739 (region 2) map units and from 0.709 to 0.728 (region 3) map units are expressed at relatively low levels and, consequently, are considered minor IE genes. Transcription under IE conditions is also detectable from another adjacent region of approximately 0.660–0.685 map units.

Developments in recombinant DNA technology have made it possible to isolate specific genes or portions thereof from higher organisms, such as man and other mammals, and to transfer the genes or fragments to a microorganism species, such as bacteria or yeast. The transferred gene is replicated and propagated as the transformed microorganism replicates. As a result, the transformed microorganism may become endowed with the capacity 1) to make whatever protein the gene or fragment encodes, whether it be an enzyme, a hormone, an antigen or an antibody, or a portion thereof or 2) to enhance or otherwise regulate such protein synthesis. The microorganism passes on this capability to its progeny, so that in effect, the transfer has resulted in a new strain, having the described capability. See, for example, Ullrich, A., et al., Science 196, 1313 (1977), and Seeburg, P. H., et al, Nature 280, 486 (1977).

A basic fact underlying the application of this technology for practical purposes is that DNA of all living organisms, from microbes to man, is chemically similar, being composed of the same four nucleotides. The significant differences lie in the sequences of the nucleotides in the polymeric DNA molecule. The nucleotide sequences are used to specify the amino acid sequences of proteins that comprise the organism. Although most of the proteins of different organisms differ from each other, the coding relationship between nucleotide sequence and amino acid sequence is fundamentally the same for all organisms. For example, the same nucleotide sequence which codes for the amino acid sequence of insulin in human pancreas cells, will, when transferred to a microorganism, be recognized as coding for the same amino acid sequence.

Abbreviations used herein are given in Table 1.

TABLE 1

| |
| --- |
| DNA = deoxyribonucleic acid |
| RNA = ribonucleic acid |
| mRNA = messenger RNA |
| A = Adenine |
| T = Thymine |
| G = Guanine |
| C = Cytosine |

Many recombinant DNA techniques employ two classes of compounds, transfer vectors and restriction enzymes, to be discussed in turn. A transfer vector is a DNA molecule which contains, inter alia, genetic information which insures its own replication when transferred to a host microorganism strain. Examples of transfer vectors commonly used in bacterial genetics are plasmids and the DNA of certain bacteriophages. Although plasmids have been used as the transfer vectors for the work described herein, it will be understood that other types of transfer vector may be employed.

Plasmid is the term applied to any autonomously replicating DNA unit which might be found in a microbial cell, other than the genome of the host cell itself. A plasmid is not genetically linked to the chromosome of the host cell. Plasmid DNA's exist as double stranded ring structures generally on the order of a few million daltons molecular weight, although some are greater than $10^8$ daltons in molecular weight. They usually represent only a small percent of the total DNA of the cell.

Transfer vector DNA is usually separable from host cell DNA by virtue of the great difference in size between them. Transfer vectors carry genetic information enabling them to replicate within the host cell, in some cases independently of the rate of host cell division. Some plasmids have the property that their replication rate can be controlled by the investigator by variations in the growth conditions.

Plasmid DNA exists as a closed ring. However, by appropriate techniques, the ring may be opened, a fragment of heterologous DNA inserted, and the ring reclosed, forming an enlarged molecule comprising the inserted DNA segment. Bacteriophage DNA may carry a segment of heterologous DNA inserted in place of certain nonessential phage genes. Either way, the transfer vector serves as a carrier or vector for an inserted fragment of heterologous DNA.

Transfer is accomplished by a process mown as transformation. During transformation, bacterial cells mixed with plasmid DNA incorporate entire plasmid molecules into the cells. It is possible to maximize the proportion of bacterial cells capable of taking up plasmid DNA and hence of being transformed, by certain empirically determined treatments. Once a cell has incorporated a plasmid, the latter is replicated within the cell and the plasmid replicas are distributed to the daughter cells when the cell divides. Any genetic information contained in the nucleotide sequence of the plasmid DNA can, in principle, be expressed in the host cell.

Typically, a transformed host cell is recognized by its acquisition of traits carried on the plasmid, such as resistance to certain antibiotics. Different plasmids are recognizable by the different capabilities or combination of capabilities which they confer upon the host cell containing them. Any given plasmid may be made in quantity by growing a pure culture of cells containing the plasmid and isolating the plasmid DNA therefrom.

Restrictions endonucleases are hydrolytic enzymes capable of catalyzing site-specific cleavage of DNA molecules. The locus of restriction endonuclease action is determined by the existence of a specific nucleotide sequence. Such a sequence is termed the recognition site for the restriction endonuclease. Restriction endonucleases from a variety of sources have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive or "sticky", and may be used to rejoin the hydrolyzed DNA.

Since any DNA susceptible of cleavage by such an enzyme must contain the same recognition site, the same cohesive ends will be produced, so that it is possible to join heterologous sequences of DNA which have been treated with restriction endonuclease to other sequences similarly treated. While restriction sites are relatively rare, the general utility of restriction endonucleases has been greatly amplified by the chemical synthesis of double stranded oligonucleotides bearing the restriction site sequence. Therefore, virtually any segment of DNA can be coupled to any other segment simply by attaching the appropriate restriction oligonucleotide to the ends of the molecule, and subjecting the product to the hydrolytic action of the appropriate restriction endonuclease, thereby producing the requisite cohesive ends.

The term "expression" is used in recognition of the fact that an organism seldom if ever makes use of all its genetically endowed capabilities at any given time. Even in relatively simple organisms such as bacteria, many proteins which the cell is capable of synthesizing are not synthesized, although they may be synthesized under appropriate environmental conditions. When the protein product, coded by a given gene, is synthesized by the organism, the gene is said to be expressed. If the protein product is not made, the gene is not expressed. Normally, the expression of bacterial genes is regulated in such a manner that proteins whose function is not useful in a given environment are not synthesized and metabolic energy is conserved.

The means by which gene expression is controlled in *E. Coli* are well understood, as the result of extensive studies over the past twenty years. See, generally, Hayes, W., *The Genetics of Bacteria And Their Viruses*, 2d edition, John Wiley and Sons, Inc., New York (1968), and Watson J. D., *The Molecular Biology of the Gene*, 3d edition, Benjamin, Menlo Park, Calif. (1976). These studies have revealed that several genes, usually those coding for proteins carrying out related functions in the cell, are found clustered together in continuous sequence. The cluster is called an operon. All genes in the operon are transcribed in the same direction, beginning with the codons coding for the N-terminal amino acid of the first protein in the sequence and continuing through to the C-terminal end of the last protein in the operon. At the beginning of the operon, proximal to the N-terminal amino acid codon, there exists a region of the DNA, termed the control region, which includes a variety of controlling elements including the operator, promoter and sequences for the ribosomal binding sites as well as enhancers. The function of these sites is to permit the expression of those genes under their control to be responsive to the needs of the organism. For example, those genes coding for enzymes required exclusively for utilization of lactose are not expressed unless lactose or an analog thereof is actually present in the medium. The control region functions that must be present for expression to occur are the initiation of transcription and the initiation of translation at the position coding for the N-terminal amino acid of the first protein from that point is also initiated in turn, at least until a termination signal or another operon is encountered with its own control region, keyed to respond to a different set of environmental cues.

Once a given gene has been isolated, purified and inserted in a transfer vector, the over-all result of which is termed the cloning of the gene, its availability in substantial quantity is assured. The cloned gene is transferred to a suitable microorganism, wherein the gene replicates as the microorganism proliferates and from which the gene may be reisolated by conventional means. Thus is provided a continuously renewable source of the gene for further manipulations, modifications and transfers to other vectors or other loci within the same vector.

SUMMARY OF THE INVENTION

In the present invention, a technique suitable for cloning a DNA molecule having a base sequence containing regulatory signals for efficient transcription in the human cell is disclosed. The invention is exemplified by the cloning of a DNA fragment containing regulatory signals and a promoter for transcription in human cells. The fragment, termed the HCMV promoter-regulatory region, is obtained from human cytomegalovirus.

Viral DNA is purified from the virus and digested with the restriction endonuclease XbaI. The XbaI DNA fragments are cloned into bacterial plasmid pACYC184. The HCMV XbaIE region is identified as a region highly transcribed in human cells immediately after infection. The XbaIE DNA is digested with the restriction endonuclease PstI and the resulting DNA fragments were cloned into bacterial plasmid pKH47. One of the above subclones (pXEP22) contains a strong promoter-regulatory region, but there remains extraneous DNA sequence on both sides of the promoter-regulatory region. Therefore, the pXEP22 clone is digested with the restriction endonuclease Sau3A and a clone designated pIEPR12 is isolated. This clone contains approximately 760 base pairs of HCMV DNA inserted into vector plasmid pAT153. Within this region is the promoter and regulatory sequence for efficient transcription in human cells.

Replication and propagation of the recombinant transfer vector containing the HCMV DNA is accomplished by transforming a host microorganism with the recombinant vector. Replication of the recombinant vector occurs in the normal course of growth and cell division of the host. The amplified cloned gene is reisolated from cell extracts of the host microorganisms using currently available techniques well known to the art. The cloned HCMV promoter-regulatory region is isolated and characterized by determining its nucleotide sequence. The purified HCMV promoter-regulatory sequence is ligated upstream of various genes such as ovalbumin, thymidine kinase, and chloramphenicol acetyl transferase. Transcription and expression of these genes is enhanced. In addition, enhancement of the HCMV promoter-regulatory component by a HCMV specified component is demonstrated.

A novel plasmid designated pIEPR12 was produced as described above. A novel microorganism, designated E. coli C600 RecBC⁻ pIEPR12 was produced by transformation with pIEPR12. The novel microorganism and the novel plasmid were placed on deposit in the United States Department of Agriculture Northern Regional Research Center (NRRL) 1815 No. University Street, Peoria, Ill. 60604, on Jan. 30, 1985. The NRRL accession number for E. coli RecBC⁻ pIEPR12 is B-15931. The accession number for plasmid pIEPR12 is B-15930.

BRIEF DESCRIPTION OF THE DRAWINGS

The accompanying figures and drawings are provided to demonstrate the results obtained in the specific examples illustrating the invention.

FIG. 1, top panel represents the nucleotide sequence for the promoter-regulatory region of the major IE gene. The sequences of the IE region 1 promoter-regulatory regions were sequenced in both directions by chemical methods as described. The numbers above the sequences represent plus or minus nucleotides from the cap site. The TATA and CAAT boxes, which are two elements that constitute the promoter, are enclosed. Relevant restriction enzymes cites are underlined and designated.

FIG. 1, bottom panel represents a sequence assay strategy for the prototype arrangement of the Towne HCMV strain. The arrow indicates the direction of sequence determination.

FIG. 3 represents the repeated nucleotide sequences in the promoter-regulatory region of the major IE gene. Residues shown in large letters conform to a consensus, whereas those shown in small letters deviate from a consensus. A central region that is highly conserved in the 18-nucleotide repeat is underlined.

DESCRIPTION OF THE PREFERRED EMBODIMENTS

Figure 2:
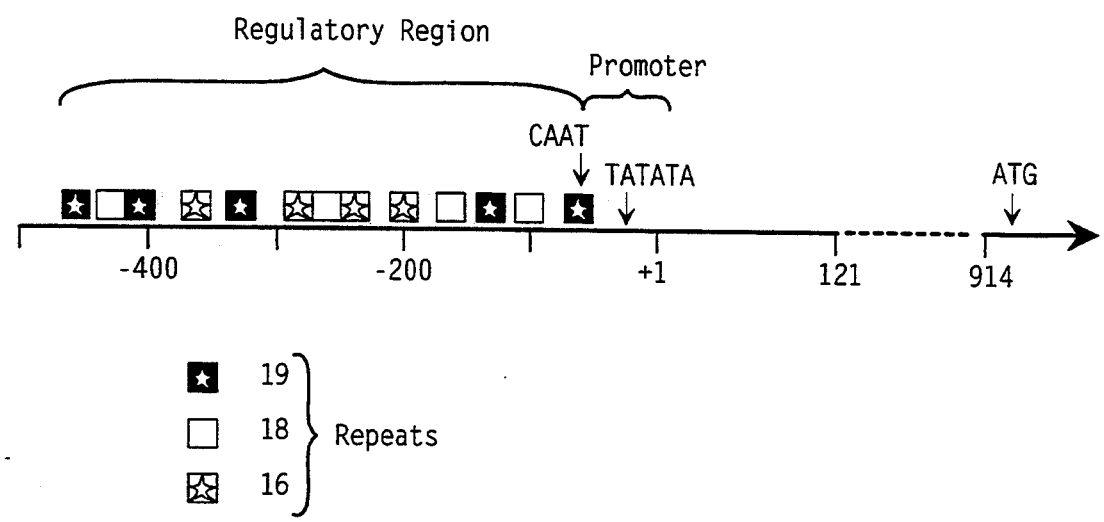
FIG. 2 is a graphical representation of the order of the 16-, 18- and 19-nucleotide repeat sequences found in the HCMV promoter-regulatory region.

The promoter contains the typical TATA and CAAT box (Chambon et al., Annual Rev. Biochem., 50:349–383, 1981). At approximately 23 nucleotides downstream from the TATA box is the initiation site for RNA synthesis. The regulatory region is defined as that sequence of nucleotides upstream from the CAAT box to approximately $-465$ nucleotides. The 5'-end of the HCMV major immediate early gene was designated $+1$ and the nucleotides upstream were designated using negative numbers according to convention.

The upstream repeat sequences play a crucial role in the level of expression of the adjacent gene. FIG. 3 shows the human CMV regulatory sequence which has characteristically three different sets of repeat sequences designated the 19n, 18n and 16n repeats. Each repeat sequence is repeated at least four times. There is a 21n repeat sequence that is repeated twice. A consensus sequence for each repeat is also shown in FIG. 3. The consensus sequence represents the nucleotides most frequently present within that particular repeat sequence. FIG. 2 graphically represents the ordering of the repeat sequences.

The repeat sequence and/or the surrounding sequences play a critical role in the relative level of expression of the downstream gene. This has been established by deleting various sections of the regulatory sequence and measuring the relative amount of downstream expression. Although the exact sequence involved in the enhancement of downstream expression is still undefined, the nucleotides between $-465$ and $+1$ play a critical role. This region is dominated by the 19n, 18n and 16n repeat sequences. Experiments using various deletions of the regulatory sequence suggest a direct correlation between the number of repeats and the relative level of gene expression. Hence, these sequences or adjacent sequences constitute a component of the regulatory region that enhances the level of expression of the adjacent gene. These components are referred to as enhancers or activators as described above.

The components in the HCMV promoter-regulatory region fit the above definition of enhancers. However, the human CMV promoter-regulatory region is unique because a component of the virus or of a noninfectious aberrant vital particle called dense bodies can enhance downstream expression. A specific region or regions of the HCMV promoter-regulatory region is required for interaction with this virus-specific component. The enhancer found in the HCMV promoter-regulatory sequence is a human cell specific enhancer component. It is currently not known whether the enhancer component is cell specific. However, it is known that recognition of the HCMV promoter-regulatory sequences by a viral component is virus-specific. For example, this enhancer-like component is not recognized by herpes simplex virus. Therefore, the HCMV promoter-regulatory sequence contains components that are acted upon both by human host cell factors and by virus-specific factors.

EXAMPLE I

DNA Sequence Analysis

Recombinant plasmid pXEP22 containing the 5'-end of the major IE RNA and as promoter-regulatory region were digested with the appropriate restriction endonucleases, fractionated by electrophoresis on agarose or acrylamide gels and eluted electrophoretically. The methods used for labeling DNA in vitro and for sequence determination by chemical modification and degradation procedure of Maxam and Gilbert (Methods Enzymol. 65:499-560) have been described (Stenberg, Thomsen and Stinski J. Virol. 49:190-199).

The nucleotides sequence shown in FIG. 1 represents the results of this structural analysis.

EXAMPLE II

Transcription Analysis

The presence of the HCMV repeat sequences facilitates transcription both in vitro or in vivo. In vitro transcription was tested with a human cell lysate (HeLa cells) prepared by the method of Manley (Proc. Natl. Acad. Sci. U.S.A. 77:3855-3859, 1980). In vivo transcription was tested by inoculating human cells with calcium phosphate precipitates of the recombinant DNA, a method referred to as transfection, extraction of the cytoplasmic RNA, and measurement of the amount of specific RNA by a Berk and Sharp analysis (Cell 12:721-732, 1977). Therefore, activation of a gene adjacent to the HCMV promoter-regulatory region is at the transcriptional level, i.e., the presence of these viral specific sequence increases the amount of transcription of the adjacent gene. There is ultimately a higher amount of mRNA available for translation in the cytoplasm. Therefore, it is proposed the HCMV regulatory sequences compete most effectively for cellular factors in the human cell that play a role in the transcription.

EXAMPLE III

Isolation of the Promoter-Regulatory Region from HCMV

The HCMV promoter-regulatory region represents a very small section (465 base pairs) of the complicated HCMV genome of 240 kilobases. The use of recombinant DNA technology enabled the isolation of this promoter-regulatory region as follows. The entire HCMV genome was cloned into bacterial plasmids by ligating XbaI digested HCMV DNA to the XbaI site of vector plasmid pACYC184 (Thomsen and Stinski, Gene 16:207-216, 1981). Transcriptional mapping studies indicate that the first genes expressed after infection of human cells by HCMV are located in the XbaIE region (Stinski et al., J. Virol. 46:1-14, 1983).

Further transcriptional mapping studies indicate there are three genes expressed immediately after infection but one gene was highly expressed in terms of level of mRNA and protein product (Stinski et al., J. Virol. 46:1-14, 1983). This gene is referred to as immediate early gene 1 or the major immediate early gene. A structural analysis of this gene determined the 5'-end of the viral mRNA as well as the 3'-end and the extent of the exons, regions included in the mRNA molecule, and introns, regions not included in the mRNA molecule (Stenberg et al., J. Virol. 49:190-199, 1984).

The XbaIE region (20 kilobases) of HCMV DNA was subcloned to isolate smaller sections of the viral DNA. This was accomplished by digesting the XbaIE DNA with the restriction enzyme PstI. A clone designated pXEP22 (2.0 kilobases) was isolated. Transcriptional mapping studies indicated this region of viral DNA contained the 5'-end of the viral gene as well as downstream and upstream sequences.

EXAMPLE IV

Isolation of the Promoter-Regulatory Region from pXEP22

The HCMV promoter-regulatory region was isolated from the pXEP22 plasmid by cutting the viral DNA with the restriction enzyme Sau3A and ligating the fragments into the bacterial vector plasmid pAT153. This clone was designated pIEPR12. The inserted viral DNA represents approximately 760 base pairs of viral DNA demarcated by the Sau3A sites at each end (see FIG. 1a). This section of DNA contains the HCMV promoter-regulatory region. Within this section of vital DNA is the Sau3A site at the 3'-end ($+7$), the initiation site for RNA synthesis ($+1$) the TATA box ($-28$), the CAAT box ($-62$), the HCMV regulatory sequences ($-62$ to approximately $-465$), a section of DNA with no known function (approximately $-465$ to approximately $-760$), and the Sau3A site at the 5'-end ($\sim -760$).

EXAMPLE V

Transformation of E. Coli

The plasmid designated pIEPR12 was used to transform bacteria E. coli C600 RecBC$^-$. This bacterial host was selected because deletions would occur in E. coli HB101 RecA$^-$. The transferred plasmid is replicated and propagated as the transformed microorganism replicates. As a result, large quantities of the HCMV promoter-regulatory region are duplicated. The microorganism passes on this capability to its progeny, so that in effect, the transfer has resulted in a new strain. The pIEPR12 recombinant DNA molecule consists of a transfer vector and the isolated HCMV viral DNA.

Separation of the pIEPR12 is based on the great difference in size and in density while in the presence of ethidium bromide. The pIEPR12 recombinant plasmid is made in quantity by growing a pure culture of cells containing the plasmid and isolating the plasmid DNA therefrom.

EXAMPLE VI

Isolation of the Promoter Regulatory-Region from pIEPR12

The HCMV promoter-regulatory region can be isolated from pIEPR12 by digestion with the restriction endonuclease Sau3A. This enzyme catalyzes hydrolysis of the DNA bond separated by a few nucleotides producing free single stranded regions at each end of the cleaved molecule. Such single stranded ends are self-complementary, hence cohesive, and may be used to rejoin the hydrolyzed DNA. Therefore, it is possible to join cohesive ends of heterologous sequences of DNA. The HCMV promoter-regulatory region with its Sau3A cohesive ends has been joined to a number of heterologous DNA cohesive ends produced by digestion with the restriction endonucleases BamHI and BglII. These restriction enzymes and some others produce ends that are complementary to the Sau3A site.

The expression of the ovalbumin gene linked to the HCMV promoter-regulatory region in proper orientation and reading frame is regulated at a low level in the stably transformed cell. However, synthesis of the ovalbumin gene can be turned on by a HCMV component. The use of the HCMV promoter-regulatory region requires the cloning of a mammalian gene. Ligation of the HCMV promoterregulatory region in proper orientation to the mammalian gene and subsequent insertion of the gene into a human cell would allow one to study expression of the gene in question. Significantly higher amounts of gene expression can be induced by adding virions (the virus particle) and/or dense bodies (an aberrant virus particle) of HCMV. Most human cells in culture, with the exception of the human fibroblast cell, do not efficiently support HCMV replication. Therefore, the infection is nonproductive but all that is required to turn on the gene is a component associated with the virus and/or dense bodies, an aberrant particle of the virus.

While the invention has been described in connection with specific embodiments thereof, it will be understood that it is capable of further modifications and this application is intended to cover any variations, uses, or adaptations of the invention following, in general, the principles of the invention and including such departures from the present customary practice within the art to which the invention pertains and as may be applied to the essential features hereinbefore set forth, and as follows in the scope of the appended claims.

I claim:

1. A transfer vector comprising the immediate-early promoter-regulatory region of human cytomegalovirus.

2. The transfer vector of claim 1 comprising a heterologous gene positioned downstream and operatively linked to said region.

3. A host cell transformed with the transfer vector of claim 1.

4. A host cell transformed with the transfer vector of claim 2.

5. A eucaryotic host cell transformed with a transfer vector comprising the immediate-early promoter-regulatory region of human cytomegalovirus and a heterologous gene positioned downstream and operatively linked to said region.

6. The transformed eucaryotic host cell of claim 5 wherein said host cell is a mammalian host cell.

7. A host cell engineered using recombinant DNA technology to contain the immediate-early, promoter-regulatory region of human cytomegalovirus.

* * * * *